United States Patent
Lechner et al.

(10) Patent No.: US 11,839,508 B2
(45) Date of Patent: Dec. 12, 2023

(54) APPARATUS AND METHOD FOR DETECTING CAVITATIONS USING THROUGH-TRANSMISSION ALVEOLAR ULTRASONOGRAPHY (TAU)

(71) Applicant: Johann Lechner, Muchen (DE)

(72) Inventors: Johann Lechner, Muchen (DE); Stefan Falcke, Muchen (DE); Bernd Zimmerman, Starnberg (DE)

(73) Assignee: Johann Lechner, Muchen (DE)

( * ) Notice: Subject to any disclaimer, the term of this patent is extended or adjusted under 35 U.S.C. 154(b) by 519 days.

(21) Appl. No.: 16/772,021

(22) PCT Filed: Dec. 10, 2018

(86) PCT No.: PCT/EP2018/084199
§ 371 (c)(1),
(2) Date: Jun. 11, 2020

(87) PCT Pub. No.: WO2019/110846
PCT Pub. Date: Jun. 13, 2019

(65) Prior Publication Data
US 2021/0068779 A1    Mar. 11, 2021

(30) Foreign Application Priority Data
Dec. 8, 2017   (DE) .................. 10 2017 011 311.4

(51) Int. Cl.
*A61B 8/08*    (2006.01)
*A61B 8/15*    (2006.01)

(52) U.S. Cl.
CPC .............. *A61B 8/0875* (2013.01); *A61B 8/15* (2013.01)

(58) Field of Classification Search
CPC ....... A61B 8/0875; A61B 8/15; A61B 5/0088; A61B 8/587; A61B 2017/00106;
(Continued)

(56) References Cited

U.S. PATENT DOCUMENTS 5,465,723 A * 11/1995 Angelsen .................. A61B 8/12
                                                    600/448
6,030,221 A *  2/2000 Jones ..................... A61B 8/0875
                                                    600/458
(Continued)

FOREIGN PATENT DOCUMENTS

CN    105030272 A    11/2015
CN    105073015      11/2015
(Continued)

OTHER PUBLICATIONS

Bouquot J.E., et al., "Computer-based Thru-transmission Sonography (CTS) Imaging of Ischemic Osteonecrosis of the Jaws—A Preliminary Investigation of 6 Cadaver Jaws and 15 Pain Patients," Oral Surgery, Oral Medicine, Oral Pathology and Oral Radiology Endodontology, 2001, vol. 92, 1 page.
(Continued)

*Primary Examiner* — Yi-Shan Yang
*Assistant Examiner* — Alexei Bykhovski
(74) *Attorney, Agent, or Firm* — Kramer & Amaodo, P.C.

(57) ABSTRACT

The present invention relates to an apparatus, method and system for detecting and locating dental cavitations in jawbones using Through-Transmission Alveolar Ultrasonography (TAU). The apparatus comprises a measuring unit comprising an ultrasonic transducer and a round ultrasonic receiver. The apparatus is a handhold and is configured to define the geometric position of the ultrasonic transducer and the ultrasonic receiver with respect to each other so as to achieve a high-resolution ultrasound image of the jawbone with minimal errors and in order to improve diagnosis of dental cavitations.

16 Claims, 3 Drawing Sheets

(58) Field of Classification Search
CPC ....... A61B 2090/378; A61B 8/12; A61B 8/42; A61B 8/4272; A61B 8/4455; A61B 8/58; A61B 1/24; A61B 8/4494; A61M 37/0092; G06T 2207/10132; G06T 2207/30036; A61C 19/04
See application file for complete search history.

(56) References Cited

U.S. PATENT DOCUMENTS

| | | | | |
|---|---|---|---|---|
| 6,364,837 | B1* | 4/2002 | Mazess | A61B 8/0875 600/449 |
| 2002/0012897 | A1 | 1/2002 | Tingley et al. | |
| 2003/0023167 | A1 | 1/2003 | Azzam et al. | |
| 2005/0070797 | A1* | 3/2005 | Cadossi | A61B 8/0875 601/2 |
| 2009/0024040 | A1* | 1/2009 | Cespedes | A61B 5/0075 600/467 |
| 2010/0210943 | A1* | 8/2010 | Mahmoud | A61B 8/4245 600/437 |
| 2014/0005521 | A1 | 1/2014 | Kohler et al. | |
| 2014/0094702 | A1* | 4/2014 | Kim | A61B 8/08 600/438 |
| 2015/0305715 | A1* | 10/2015 | Tan | G01S 7/52077 600/443 |
| 2016/0011305 | A1* | 1/2016 | Koptenko | G11C 27/024 367/7 |
| 2016/0081656 | A1* | 3/2016 | Abraham | A61B 8/582 600/439 |
| 2016/0157820 | A1 | 6/2016 | Han | |
| 2016/0157833 | A1 | 6/2016 | Smith et al. | |
| 2016/0209502 | A1 | 7/2016 | Kim et al. | |
| 2017/0003384 | A1 | 1/2017 | Christiansen et al. | |
| 2017/0103534 | A1* | 4/2017 | Park | A61B 8/4405 |
| 2017/0119425 | A1* | 5/2017 | Hibner | A61B 90/03 |
| 2017/0196541 | A1 | 7/2017 | Boon | |
| 2019/0059930 | A1* | 2/2019 | Stulen | A61B 34/30 |
| 2019/0223759 | A1* | 7/2019 | Page | A61B 34/35 |
| 2019/0251327 | A1* | 8/2019 | Laviola | A61B 8/5261 |

FOREIGN PATENT DOCUMENTS

| | | |
|---|---|---|
| CN | 105939673 A | 9/2016 |
| CN | 106725604 A | 5/2017 |
| EP | 2 939 590 A1 | 11/2015 |
| JP | 2009-50560 A | 3/2009 |
| JP | 2016522709 A | 8/2016 |
| JP | 2017505168 A | 2/2017 |
| WO | 03/053247 A1 | 7/2003 |
| WO | 2005/034785 A2 | 4/2005 |
| WO | 2017/177096 A1 | 10/2017 |

OTHER PUBLICATIONS

Bouquot J.E., et al., "Neuralgia-Inducing Cavitational Osteonecrosis (NICO), Osteomyelitis in Jawbone samples from Patients with Facial Neuralgia," Oral Surgery, Oral Medicine and Oral Pathology, 1992, vol. 73 (3), pp. 307-319.

Imbeau J., "Introduction to Through-Transmission Alveolar Ultrasonography (TAU) in Dental Medicine," The Journal of Craniomandibular Practice, 2005, vol. 2 (23), pp. 100-112.

International Preliminary Report issued in International Application No. PCT/EP2018/084199, dated Jun. 9, 2020, 13 pages.

Klein M.O., et al., "Ultrasound Transmission Velocity for Non-Invasive Evaluation of Jaw Bone Quality in vivo prior to Dental Implantation," Ultrasound in Medicine & Biology, 2008, vol. 34, pp. 1966-1971.

Langton C. M., et al., "The Measurement of Broadband Ultrasonic Attenuation in Cancellous Bone—A Review of the Science and Technology," IEEE Transactions on Ultrasonic, Ferroelectrics, and Frequency Control, 2008, vol. 7(55), pp. 1546-1554.

Lechner J., "Aseptic-Avascular Osteonecrosis: Local 'Silent Inflammation' in the Jawbone and RANTES/CCL Overexpression," Clinical, Cosmetic and Investigational Dentistry, 2017, vol. 9, pp. 99-109.

Lechner J., "Rantes and Fibroblast Growth Factor in Jawbone Cavitation's: Triggers for Systemic Disease," International Journal of General Medicine, 2013, vol. 6, pp. 277-290.

Lechner J., "Validation of Dental X-ray by Cytokine Rantes—Comparison of X-ray findings with Cytokine Overexpression in Jawbone", Clinical, Cosmetic and Investigational Dentistry, 2014, No. 6, pp. 71-79.

Written Opinion issued in International Application No. PCT/EP2018/084199, dated Sep. 17, 2019, 12 pages.

German Search Report dated Oct. 10, 2018 in corresponding German Application No. 10 2017 011 311.4.

International Search Report dated Sep. 17, 2019 in connection with related International Application No. PCT/EP2018/084199, filed Dec. 10, 2018.

Lechner, et al., "Immune messengers in Neuralgia Inducing Cavitational Osteonecrosis (NICO) in jaw bone and systemic interference", European Journal of Integrative Medicine, vol. 2, Issue 2, pp. 71-77. (Jun. 2010).

Notice of First Office Action dated Apr. 21, 2021 re Application/Patent No. 2018800872976; 9 pgs.

Translation of First Office Action dated Apr. 21, 2021 e Application/Patent No. 2018800872976; 8 pgs.

Translation of CN 105073015 A; CN105073015A—Coupling structures for an ultrasound probe—Google Patents; Jun. 29, 2021; 13 pgs.

Notice of Reasons for Refusal for Japanese Patent Application No. 20200550913, dated Sep. 22, 2022, 6 pages.

* cited by examiner

APPARATUS AND METHOD FOR DETECTING CAVITATIONS USING THROUGH-TRANSMISSION ALVEOLAR ULTRASONOGRAPHY (TAU)

FIELD OF THE INVENTION

The invention relates to an apparatus and method for detecting and locating cavitations. Specifically, the invention relates to detecting and locating dental cavitations in jawbones using Through-Transmission Alveolar Ultrasonography (TAU).

BACKGROUND OF THE INVENTION

In the medical field in general, pulse-echo ultrasonography is widely used for imaging all kinds of soft tissue. In principle, images from structures inside the body are produced by analyzing the reflection of ultrasound waves. This method however is not suitable to yield useful information on the status of the jawbone because of almost complete reflection of ultrasound at the bone/soft tissue interphase. Particularly the cancellous part of the jawbone cannot be examined with commonly used ultrasound equipment. Thus, up to now ultrasound is of very limited use in dental medicine. An exception might be the PhD thesis of Cora Freyse from Rostock (Germany) where the possibilities to determine defects in the hard tissue, e.g. defects at the border of a filling and the natural tooth tissue, using reflection of ultrasound waves, is investigated (cf. http://www-.deutschlandfunkkultur.de/zaehne-ultraschall-statt-strahlen.1067.de.html?dram:article_id=289091).

The status of the cancellous bone of the jaws can be clinically of great importance. Jerry Bouquot has provided anatomical evidence that the cancellous bone can be largely degenerated, a phenomenon which he calls inter alia "ischemic osteonecrosis leading to cavitational lesions". He relates osteonecrosis of the jawbone to neuralgic pain and defines a disease called "neuralgia inducing cavitational osteonecrosis (NICO)" (cf. J. E. Bouquot, A. M. Roberts, P. Person and J.Christian, "Neuralgia-inducing cavitational osteonecrosis (NICO). Osteomyelitis in 224 jawbone samples from patients with facial neuralgia", Oral Surg Oral Med Oral Pathol. 1992, 73 (3):307-319; J. Bouquot, W. Martin and G. Wrobleski "Computer-based thru-transmission sonography (CTS) imaging of ischemic osteonecrosis of the jaws—a preliminary investigation of 6 cadaver jaws and 15 pain patients", Oral Surg Oral Med Oral Pathol Oral Radiol Endod. 2001, 92: 550.)

Johann Lechner investigated in depth the tissue in such lesions which appears as a clump of fat inside of an intact cortical bone. During surgery the material is simply spooned out. This tissue is in an ischemic, fatty degenerative state. Lechner therefore defines the observed changes as "fatty-degenerative osteolysis/osteonecrosis of jawbone (FDOJ)". He showed that the clumps of fat found in the jawbone are biochemically exceedingly active, producing certain zytokines in high amounts, namely RANTES (CCL-5) and FGF-2, but also PDGF and MCP-1. The level of those zytokines is also elevated in a number of systemic diseases such as cancer, dementia, multiple sclerosis or arthritis. There is strong evidence—coming from startling clinical improvements after the surgical elimination of such tissue—that the development and the persistency of a variety of systemic diseases can be related to the fatty-degenerative osteolysis of jawbone (FDOJ). However, in most of these cases the local effect of neuralgic pain (NICO) is missing. (Cf. J. Lechner and V. von Baehr, "RANTES and fibroblast growth factor 2 in jawbone cavitations: triggers for systemic disease?" International Journal of General Medicine 2013, 6: 277-290; J. Lechner and W. Mayer "Immune messengers in neuralgia inducing cavitational osteonecrosis (NICO) in jaw bone and systemic interference", Eur. J. Integr. Med. 2010, 2 (2): 71-77.)

Furthermore, in a recent publication it was made plausible that NICO and FDOJ as well as the so called "aseptic ischemic osteonecrosis in the jawbone" (AIOJ) all describe the same pathological condition of the jawbone which is listed under Code M87.0 in the International Statistical Classification of Diseases and Related Health Problems, tenth revision (ICD-10). (Cf. J. Lechner, S. Schuett and V. von Baehr, "Aseptic-avascular osteonecrosis: local 'silent inflammation' in the jawbone and RANTES/CCL5 overexpression", Clinical, Cosmetic and Investigational Dentistry 2017:9 99-109.)

Additionally, the status of the cancellous part of the jawbone is of great importance for dental implants and for the success of implantology, according to earlier publications of Bilal Al-Nawas. (Cf. M. O. Klein, K. A. Grotz, B. Manefeld, P. H. Kann and B. Al-Nawas, "Ultrasound transmission velocity for non-invasive evaluation of jaw bone quality in vivo prior to dental implantation", Ultrasound in Medicine & Biology 2008, 34: 1966-1971.)

Hence, serious health risks can be associated with fatty-degenerative osteolysis of the jawbone. A major problem however is that a jawbone with fatty-degenerative osteolysis appears without abnormal findings in X-ray examination. This holds true even if the cancellous bone is in a largely degenerated status, showing only fatty tissue instead of the substantia spongiosa of healthy cancellous bone (FDOJ). Being virtually undetectable by any kind of X-ray examination the occurrence and the phenomena of AIOJ, FDOJ and NICO remain widely unknown and even are disputed or denied (cf. J. Lechner, "Validation of dental X-ray by cytokine RANTES—comparison of X-ray findings with cytokine overexpression in jawbone", Clinical, Cosmetic and Investigational Dentistry 2014, 6: 71-79.)

To overcome the aforementioned problem, a different approach was needed. Instead of X-ray or other established medical examination methods the use of Through-Transmission Alveolar Ultrasonography (TAU) was evaluated.

Transmission Ultrasonography is well known in some technical fields such as the aircraft industry, e.g. for the examination of welding seams. But it also used in the medical field for the determination of bone densities for the diagnosis of osteoporosis (cf. C. M. Langton and C. F. Njeh. "The Measurement of Broadband Ultrasonic Attenuation in Cancellous Bone—A Review of the Science and Technology", IEEE Transactions on Ultrasonics, Ferroelectrics, and Frequency Control, 2008 (55) 7: 1546-1554.)

U.S. Pat. No. 6,030,221 A is believed to be the first disclosure of a Through-Transmission Alveolar Ultrasonography (TAU) apparatus for detecting jawbone cavitations. This TAU apparatus generates an ultrasound pulse and passes the pulse through the jawbone of a patient. The pulse is detected and monitored subsequently by an ultrasound receiving unit. Attenuations of the amplitude of the pulse are indicative for pathological changes in the jawbone. The results are displayed on a color monitor, showing different colors according to different degrees of attenuation.

The TAU apparatus corresponding to the disclosure of U.S. Pat. No. 6,030,221 A was commercially available for a couple of years. It was the Cavitat Ultrasonograph CAV 4000, developed by engineers at Cavitat Medical Technologies. This known TAU apparatus used a plurality of receiving elements, wherein the frequency of the output pulse and that of the sound wave were in the range of about 2.5 MHz. The processing of the received sound wave was performed by a digitizer having an operating frequency of about 100 MHz. Jacques Imbeau describes in more detail the underlying principles and the work with this apparatus in the publication J. Imbeau, "Introduction to Through-Transmission Alveolar Ultrasonography (TAU) in Dental Medicine", The Journal of Craniomandibular Practice, 2005 (23) 2: 100-112.

However, the TAU apparatus according to the prior art shows considerable drawbacks which are explained in more depth by Imbeau, ibid. page 106/107. These drawbacks are:

First, the correct and reproducible placement of the sensor and of the transducer—in respect to the anatomical structures involved—affords a considerable amount of skill and experience making the technique rather susceptible and difficult, so that i.a. Imbeau calls TAU a "user sensitive technique" (Imbeau, ibid. page 105). Correspondingly, the reproducibility of the measurements was rather low. Furthermore, the intricate problem of air bubbles in the ultrasonic gel used is already mentioned by Imbeau; air bubbles falsify in an unpredictable way the ultrasonic signals which pass through a medium, in this case through a jawbone.

Second, the signals coming from the receiving elements of the Cavitat Ultrasonograph were very weak. The evaluation of these signals was therefore a very demanding task. Due to this the sensitivity of the TAU apparatus was not very great. Furthermore, the method of signal analysis is not disclosed in U.S. Pat. No. 6,030,221A (cf. Imbeau, ibid. page 104).

Third, the construction of the ultrasound receiving unit of the Cavitat Ultrasonograph was not sufficiently sturdy such that, during use, more of the individual measuring units of the receiving unit broke, whilst concomitantly spare parts were no longer available as the manufacturer, Cavitat Medical Technologies, had been out of business for some time. Hence, the technology became less accessible.

Fourth, for the user there was no possibility to check the calibration of the TAU apparatus regularly over the course of time.

The present invention overcomes the one or more or all of the aforementioned drawbacks.

SUMMARY OF THE INVENTION

The present invention provides a new TAU apparatus comprising an ultrasonic transducer and an ultrasonic receiver, which are called hereafter the "measuring unit", and are arranged in a fixed geometrical position to each other, preferably in a coplanar manner.

As compared to the state of the art the construction of the receiver is greatly improved (i) the number of active piezoelectric elements is increased and (ii) the broad circular area (without any active piezoelectric elements) which hitherto surrounds the central area (with the active piezoelectric elements) is minimized to a very small rim.

The size of the new measuring unit is such that it can easily be introduced into the mouth of a patient. During the ultrasonic measurements the jawbone has to be positioned between the two parts of the measuring unit.

One part of the measuring unit, preferably the ultrasonic transducer, can be used inside or outside of the mouth of the patient, whereas the other part of the measuring unit, preferably the ultrasonic receiver, has to be inside of the mouth on the lingual or palatal side. In case of the outside positioning a conventional ultrasonic gel can be used to ensure good acoustical conductivity.

For all parts of the measuring unit that are to be placed inside of the patient's mouth the acoustical coupling between respective parts of the measuring unit and the alveolar ridge is performed either (i) with the aid of a semi-solid gel or (ii) with a flexible cover for respective parts of the measuring unit whereupon the cover is filled with a suitable medium, e.g. a conventional ultrasonic gel or preferably water in such a way that sufficient flexibility of the cover is still given ("expedient filling") or (iii) with a very flexible and elastic balloon, filled with a suitable medium, a conventional ultrasonic gel or preferably water or (iv) with the aid of the tongue of the patient. Not preferred but nevertheless possible is (v) the use of conventional ultrasonic gels.

All embodiments are suitable to equalize varying distances between the alveolar ridge and the flat plane of the corresponding part of the measuring unit. All embodiments described above allow fast adjustment of the position of the measuring unit in order to get optimized results.

DETAILED DESCRIPTION OF PREFFERED EMBODIMENTS OF THE INVENTION

Figure 1:
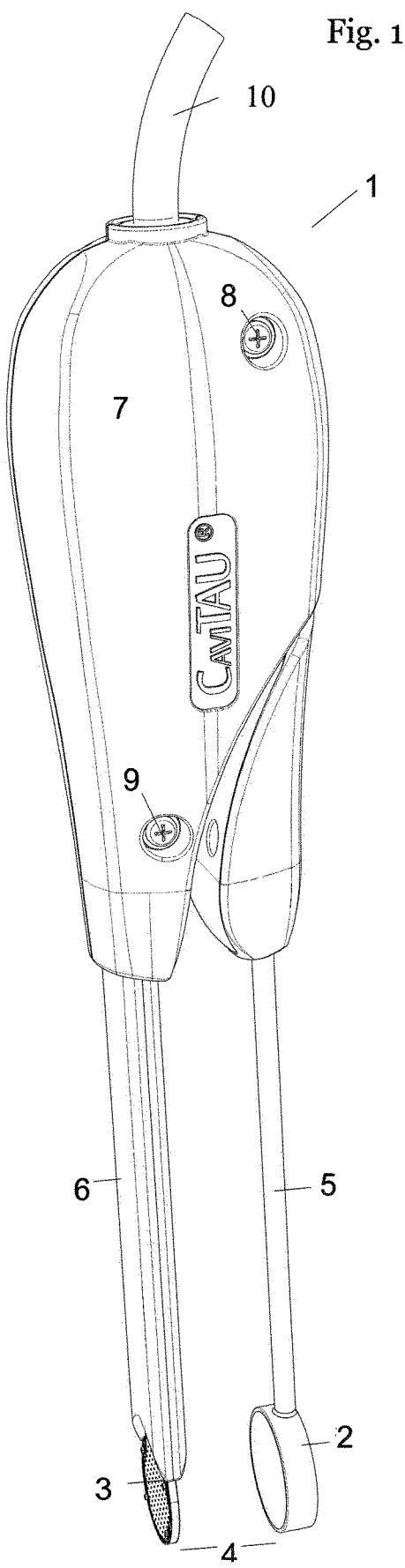
FIG. 1 shows a preferred exemplary embodiment of the invention. The apparatus 1 is a handhold. The thick round element on the left, located below, is the ultrasonic transducer 2 and the thin round element on the left, located above, is the ultrasonic receiver 3. Together they form the measuring unit 4. Two arms 5 and 6, holding the measuring unit 4, connect to the handle 7 on the right. The handle is furnished with two screws 8 and 9—the screw on the right 8 shows the position of a pivotal point for the movement of the arms 5 and 6; the screw in the middle 9 indicates the position of a blocking element which is located between the two screws but not visible in the figure. An electrical cable 10 in the rightmost position connects to the processing unit (not shown).

The Cavitat Ultrasonograph represents the closest state of the art (U.S. Pat. No. 6,030,221 A) which however shows a couple of drawbacks, vide supra.

The invention discloses ways to overcome these drawbacks. However some technical features of the Cavitat Ultrasonograph are not changed, for example the frequency of the output pulse, being in the range of about 2.5 MHz. This enhances the comparability of the results of the Cavitat apparatus and of the TAU apparatus of the invention.

It is therefore an object of the invention to provide an apparatus and a method which is safer and easier to handle than the known Cavitat Ultrasonograph, so that without the need of a thorough and intensive training reproducible results can be obtained even by less experienced users.

A further object of the invention is to enhance the sensitivity of the apparatus and of the method used, in order to get more precise and more informative measurements.

Another object of the invention is a construction of the receiving unit which is robust enough to remain fully functional under the conditions of everyday use.

Finally, an object of the invention is the possibility of a calibration of the apparatus.

The foregoing objects have been achieved by a new construction of the measuring unit and by new ways to ensure good acoustical conductivity between the jawbone of the patient and the apparatus.

a) The Measuring Unit of the Invention

According to the invention, the measuring unit for enoral ultrasonic measurements, i.e. inside of the mouth, comprises an ultrasonic transducer and an ultrasonic receiver, i.e. the "measuring unit", in a clearly defined, fixed geometrical position to each other.

In the TAU apparatus according to an embodiment of the invention, the measuring unit is preferably positioned in a coplanar manner.

To provide a clearly defined, fixed geometrical position the two parts of the measuring unit are preferably fastened to or they are preferably part of two rigid arms, which are connected by a connecting element. At least one arm is rotatable so that the two parts of the measuring unit form a gripper. It is preferred to provide additionally a guidance element between pivotal point and measuring unit to avoid shearing movements of the two parts of the measuring unit against each other. Through the use of rigid arms the construction of the measuring unit is sturdy to such an extent that a malfunction of the receiver caused by mechanical strain is virtually excluded.

For the ease of handling it is preferred to provide the two rigid arms in a cranked fashion. The complete device, consisting of the ultrasonic transducer and receiver, the two rigid arms and the connecting element, is called hereafter "handhold".

According to the invention another possibility to realize a fixed geometrical position of the measuring unit may include a U-shaped device. This device consists of a centrally located bar and of transducer and receiver, being arranged vertical to the bar as side elements. Transducer and receiver are movable horizontally along the bar and are additionally relocatable in the vertical direction. The distance of transducer and receiver is immediately determined by the actual adjustment of the device. Coplanarity of transducer and receiver is an inherent feature of such a construction. Adjusting the device in the horizontal direction brings transducer and receiver close to the jawbone whereas the vertical adjustment serves to perform the measurements in the medically important jawbone region.

A handhold is possible as well, which carries at its end such a U-shaped device; thus the two possibilities described above are combined.

In the following, only the solution using a handhold is discussed.

The measurement according to the invention is performed by positioning the two arms of the device on both sides of the jawbone in the region where the existence of a cavitation is suspected or searched for. The handhold, forming a gripper, is slightly compressed when both parts of the measuring unit are in the optimal position for measurements to ensure acoustical conductivity between measuring unit and the jawbone by means which are disclosed below.

One part of the measuring unit, preferably the transducer is either on the outside somewhere on the cheek or inside on the buccal side of the mouth whereas the receiver is to be positioned on the lingual or palatal side. In both cases the position of transducer and receiver is well defined in a safe and simple way. No special training is needed to perform the measurement and due to the defined geometry optimal results are obtained.

In most cases the flexibility of the cheek is sufficient to equalize existing anatomical peculiarities and still to be able to achieve coplanarity; if not, it is possible to use a semi-solid gel, being described below. However, sometimes all this cannot be realized and some deviations from coplanarity have to be accepted although they should be kept as small as possible. It should be noted that the deviations from coplanarity occur only in one dimension whereas for the Cavitat Ultrasonograph the deviations occur routinely in all three dimensions.

One design measure according to the invention to minimize deviations from coplanarity is the following: By placing the pivotal point of the two arms of the handhold as far as possible away from transducer and receiver, only a small angle is needed to equalize pronounced anatomical features; thus, only slight deviations from coplanarity prevail. In practical work deviations from coplanarity occasionally are found to be in the range from 3° to 6°; the effects of the deviation from coplanarity can be monitored experimentally.

Because of the preferred inclusion of a displacement transducer in the handhold the angle between ultrasonic transducer and receiver can be determined exactly and occasional deviation from coplanarity can be accounted for in the analysis of the signals coming from the receiver.

More sophisticated construction methods may encompass the use of small hinges as part of the two arms of the handhold. Such construction methods allow an adaptation of the measuring unit to given anatomical conditions as well. However, under such circumstances the distance of the two parts of the measuring unit and their relative positioning gets obscured so that other determination methods for distance and angle are needed which, however, are accessible to the man skilled in the art.

Where the measuring unit itself is rigid, i.e. without rotatable elements, no compression is possible to create the needed acoustical conductivity. In this case the so called "Flexible-Cover solution" and the "Balloon solution" being described below, can be modified: first the flexible cover or the balloon have to be introduced to the measuring site and suitable means, e.g. a little pump being attached either to the cover or to the balloon, have to be used afterwards to inflate the cover or the balloon so that enough pressure is created to ensure good acoustical conductivity.

In contrast, U.S. Pat. No. 6,030,221 (the Cavitat Ultrasonograph) did not have a rigid mechanical connection between ultrasonic transducer and receiver so that the two parts of the measuring unit had to be used in a free-hand manner. The only connection between transducer and receiver consisted of the electrical wires leading to the electronic processing unit (see U.S. Pat. No. 6,030,221).

b) Improving the Sensitivity of the Apparatus

To improve the sensitivity of the new TAU apparatus as compared to the known Cavitat apparatus, two measures have been taken which are already discussed above—(i) the number of active piezoelectric elements is increased and (ii) the broad circular area (without any active piezoelectric elements) which hitherto surrounds the central area (with the active piezoelectric elements) is minimized to a very small rim. The minimum width of that rim is half the size of an active piezoelectric element. This very small rim allows measurements in anatomical structures which are inaccessible for the known Cavitat apparatus.

The use of more than 90 piezoelectric elements is preferred which furthermore should be arranged hexagonally. In addition to these measures an apodized configuration of the transducer is applied in order to reduce diffraction edge effects and to improve resolution.

c) Calibration and Functional Test

The arrangement of the measuring unit in a defined geometry allows an easy test of the functionality and calibration of the apparatus. For this purpose two or more media with different acoustical properties are provided and measurements are performed successively in these media. The use of a phantom for calibration purposes is feasible as well.

In the following example the use of water and air as media are explained but other choices of media are possible as well. Immersing completely the measuring unit in water, gradually moving the unit through the surface of the water and finally placing the unit entirely in air, while continuously sending ultrasonic signals through the unit, allows the assessment of the functionality of the apparatus. Water and air give very different signals and their expected occurrence, particularly when the measuring unit is moved through the boundary between water and air, allows the proof of the correct functioning of the apparatus. This check should be performed every time before use.

d) Securely Providing Good Acoustical Conductivity

According to U.S. Pat. No. 6,030,221 and according to the invention the part of the measuring unit (ultrasonic transducer or receiver) outside of the mouth needs only a small amount of a usual ultrasonic gel in order to achieve good acoustic conductivity.

For technical measurement reasons the arrangement of the measuring unit is ideal if—according to the invention—a clearly defined position of transducer and receiver can be achieved.

However the practical application of enoral ultrasonic measurements (i.e. in the mouth of a patient) with a fixed geometrical position of transducer and receiver, proved to be difficult. The ultrasonic gel used according to U.S. Pat. No. 6,030,221 being inside the mouth of the patient turned out to be the main obstacle in the attempt to obtain signals from through-transmission alveolar ultrasonography (TAU) in an easy and above all in a reproducible manner.

This has several reasons.

First it is difficult to keep the ultrasonic gel used free from any kind of air bubbles, because of the high viscosity of the gel. Air bubbles inhibit reliable and repeatable measurements.

Second the anatomical contour of the jawbones at the measuring site and the plane surface of the measuring unit (normally the receiver) do not fit at all. The distance between the surface of the measuring unit and the surface of the alveolar ridge varies widely, up to approximately 5 mm, so that large amounts of the coupling gel have to be applied to completely fill the gap and to get good acoustical conductivity in the entire measurement area, a fact which is expensive for the user and very unpleasant for the patient.

Third, applying such large amounts of the gel again demands that the gel has to be kept completely free from air bubbles, a condition which is difficult to fulfill in reality.

Fourth the gel has to stay in place but this happens normally only for a restricted period of time. Gradually the gel disappears somewhere inside of the mouth of the patient. Therefore the gel has to be replenished frequently; this creates even more the problem to keep the gel free from air bubbles because the visual inspection of the gel for the absence of air bubbles inside the mouth is very difficult.

Fifth in case that accidentally the alveolar ridge is only partly covered by the gel and/or that accidentally air bubbles are entrapped within the gel, the TAU apparatus does not deliver any warning signs but continues to display ultrasonic images which however are pure artefacts without any pathophysiological meaning and of course being free from repeatability. The occurrence of artefacts and the absence of warning signs represent the most intricate problems of the TAU measurements up to now.

A very experienced user of the known Cavitat Ultrasonograph could partially cope with these problems just because of the non-rigid arrangement of transducer and receiver by tilting the receiver. By tilting the receiver the amount of gel needed can be kept smaller and the problems with the handling of the gel can be reduced to some extent.

However, the uncertainty of the relative positioning of transducer and receiver created hereby is another cause for reduced repeatability and reliability of the measurements with the Cavitat Ultrasonograph, as described above and problems caused by the properties of the gel still persist.

On the other hand such a loophole is not accessible according to the invention because tilting is not possible, being prevented by the fixed geometrical position of transducer and receiver. The abovementioned possibilities to deviate from the coplanar arrangement alleviate only some of the problems with the gel. But the problematical handling of the commonly used ultrasonic gel still represents a major issue; it is the main reason for the user-dependency and the partial unreliability of the TAU measurements.

Hence, instead of the ultrasonic gel used hitherto another acoustical medium is needed with the following properties: (i) no interference of the acoustical properties of the medium with the proper measurements, (ii) optimal acoustical conductivity between the measuring device, normally the receiver, and the alveolar ridge by securing the absence of air bubbles in the acoustical medium used and by providing full and permanent contact of the medium with both, the receiver and the alveolar ridge, (iii) easy adjustability of the position of the measuring unit without disturbing the measurement and (iv) no tendency of the medium to disappear somehow during or even before the measurements.

Inside of the mouth an additional ultrasonic gel is dispensable because of the presence of the saliva in the mouth. The saliva is sufficient for good acoustical conductivity and air bubbles can easily be eliminated because of the low viscosity of saliva.

The invention discloses four solutions. (For the ease of argumentation in the following only the work with that part of the measuring unit is discussed which is located inside of the mouth; preferably this is the ultrasonic receiver.)

1. The Semi-Solid Gel Solution

In this solution a semi-solid gel is placed between receiver and alveolar ridge. The sound velocity in this gel should be in the same range as that of soft tissue i.e. 1460-1615 m/s and the gel should have a sound attenuation from 0.3-1.5 dB/cm (1 MHz) so that the acoustical measurements of the properties of the jawbone are not impeded. The haul-off speed for spontaneous resilience should be at most 80 mm/sec.

Appropriate semi-solid gels must be soft, very resilient and very flexible so that a complete contact of the semi-solid gel with the receiver and the alveolar ridge can be secured; the absence of air bubbles within the semi-solid gel used can be checked by visual inspection. Because of the flexibility of the gel it is also possible to adjust the position of the measuring unit without disturbing the contact of the gel and without disturbing the measurements. The semi-solid property of the gel prevents that the gel disappears before or during the measurement. Semi-solid gels with such characteristics are commercially available, e.g. the Sonogel Sonokit soft, article number 6510 and 6520, marketed by Sonogel Vertriebs-GmbH in Bad Camberg, Germany. It is a styrenic block copolymer with a hydrogenated midblock of styrene-ethylene/butylene-styrene or styrene-ethylene/propylene-styrene and belongs to the compound class of thermoplastic elastomers.

The semi-solid gel can be used as such and is inserted between receiver and alveolar ridge to perform the measurements. In case of complicated anatomical conditions it can be reasonable to use the semi-solid gel on the cheek, i.e. outside of the mouth, as well. In such cases, the balloon solution vide infra can be used equally.

This works well for the mandibula, whereas for the maxilla some practical skills are necessary to keep the gel in place. The gel can be held manually or it can be supported by a little auxiliary construction. The size of the piece of the semi-solid gel used should large enough to safely cover all relevant parts needed for the measurements.

In a preferred version of the invention, a piece of the semi-solid gel is fixed to the receiver. For this purpose a block of the gel is cut at the narrow side to create a little pocket into which the receiver can be inserted; the use of a very small amount of a lubricant, e.g. the formerly used ultrasonic gel or water facilitates the insertion of the receiver. After elimination of any air bubbles between the receiver and the semi-solid gel the measuring unit is ready for use.

2. The Flexible-Cover Solution

In this solution a flexible cover, which eventually is also elastic, is fastened to the measuring unit only on the side where the piezoelectric elements are located. To perform the measurements a liquid filling is inserted into the cover. As liquid a normal coupling gel can eventually be used but simply water is preferred. The presence of air bubbles has to be avoided carefully. The amount of liquid has to be such that the cover is still flexible and can be squeezed easily into any direction. The filling degree is called "expedient filling" because a tightly filled cover is not applicable for the intended measurements. During operation the receiver with the filled cover is squeezed against the alveolar ridge so that any air bubbles between cover and ridge are eliminated and a good acoustic conductivity is achieved.

The backside of the measuring unit (receiver) should not be connected to the front side in order to prevent the filling from moving, actually from disappearing, to the backside under the slight pressure which has to be applied during the measurements. The flexible cover can be clipped from the backside or it can be fastened by a rigid mask on the backside or it might be glued or laminated to the front side only. Care has to be taken that the backside of the receiver remains free from reflective layers which otherwise would create interfering signals. The provision of a damping layer is advisable.

In a preferred version of the invention the flexible cover consists of three layers that form two pockets. The three layers are closed on three sides whereas the fourth side is kept open for manipulation of the cover and can be closed afterwards.

Two layers form a narrow pocket into which the receiver can be inserted; the receiver is then connected acoustically to the cover for example by applying a tiny amount of an ultrasonic gel inside of that pocket which for the rest can be left open.

The layer on the front side of the receiver forms the middle layer of the three-layer arrangement. The third layer is placed above this middle layer and together they form the second pocket, the actual cover, into which the liquid filling is introduced. The size of the cover is not critical but has to be at least that big that all parts needed for the measurements are safely covered. Again care has to be taken that the filling is an "expedient filling". After closing the open end at least of the second pocket a device is created which establishes the possibility for reliable and easy to perform measurements.

The three-layer cover can be realized as a one-way article where the "expedient filling" is already done beforehand and, prior to use, the user only has to insert the receiver into the small pocket being left open.

Another preferred embodiment of the invention is a cover consisting of four layers. Two layers serve to form the pocket for the receiver, vide supra. Two further layers serve to form the cover which is designated to hold the filling (expedient filling). After properly connecting the two pockets the flexible cover is ready. Again it can be used after inserting the receiver and the filling.

3. The Balloon Solution

This solution uses a separate, very flexible balloon filled with an ultrasonic gel or preferably with water, being placed between the part or the parts of measuring unit inside of the patient's mouth and the alveolar ridge. To ensure good acoustical conductivity, the balloon is completely filled with the ultrasonic medium used in such a manner that it is still possible to squeeze the balloon into any direction; no air should be inside of the balloon. The size of the balloon in the filled state is not critical and should be such that it has at least the size of the measuring unit, in most cases of the receiver, to make sure that after squeezing the balloon will completely fill the space between the measuring unit and the alveolar ridge so that all parts needed for the measurements are safely covered.

During the measurements the squeezing of the filled balloon is performed by the ultrasonic transducer and ultrasonic receiver which form two parts of the measuring unit which are positioned in a predominantly or completely coplanar position to one another. Squeezing the balloon eliminates all air bubbles which might be entrapped in the space between the balloon and the alveolar ridge or the receiver. This solution works well for measurements of the mandibula. Measurements of the maxilla have the problem that the balloon drops down because of the gravity. The dropping down however can easily be prevented by supporting the balloon with a small flat device positioned from below. The small device itself can be fastened to the rigid arm of the measuring unit. The preferred use of water in the balloon avoids any disturbances of the ultrasonic signals measured because of the perfectly fitting ultrasonic properties of water.

4. The Tongue Solution

In this solution the tongue of the patient is slightly squeezed between the measuring unit and that part of the jawbone, lingual or palatal, which has to be examined by TAU, thus providing good acoustical conductivity. The acoustical properties of the tongue are known and do not interfere with the measurements of the cancellous part of the jawbone. Any air bubbles are squeezed out of the interfaces between measuring unit and tongue as well as between tongue and alveolar ridge and cannot interfere with the measurements.

This variant is technically very easy but sometimes quite uncomfortable for the patient.

e) Further Embodiments

For hygienic and for economic reasons the use of single-use covers is provided which advantageously keep the measuring device or the semi-solid gel or the flexible cover or the balloon clean and reusable. Furthermore, the single-use cover does not interfere with the flexible properties of the media used and therefore, as often found in ultrasonic measurements, a non-elastic but flexible plastic film is used, being filled inside with a very small amount of a suitable lubricant, e.g. a usual ultrasound gel so that the measuring device, the semi-solid gel, the flexible cover or the balloon can move freely inside of the cover. In case of the flexible cover solution, the use of a further single-use cover is not essential when the flexible cover itself is used as a single-use article.

In further embodiments of the invention, one or more light-emitting diodes (LEDs) are provided in order to improve the position recognition of the receiver. Furthermore, one or more cameras may also be used in order to document the position of the ultrasonic transducer and/or ultrasonic receiver during performance of the measurements. As an alternative, or in addition to the camera, an attitude sensor is provided in order to determine the orientation of the ultrasonic. All measures can be taken separately or combined.

ADDITIONAL PREFERRED EXAMPLES OF THE INVENTION

According to one aspect of the invention according to FIG. 1, an apparatus 1 is provided comprising a measuring unit 4 for performing TAU for locating cavitations in a jawbone, wherein the measuring unit comprises an ultrasonic transducer 2 and a rounded ultrasonic receiver 3. The shape of the ultrasonic receiver 3 is illustrated in FIG. 1 as being annular, however, in other implementations, it could have a different shape such as a hexagon with rounded corner points. According to the invention, the apparatus is portable i.e. hand-held and configured to define the geometric position of the ultrasonic transducer and the ultrasonic receiver with respect to each other.

In preferred examples, the ultrasonic transducer and the ultrasonic receiver each define a plane and the apparatus is further configured to arrange the respective planes in positions substantially opposite and/or substantially facing each other, wherein, during use, the planes are substantially parallel to each other, preferably at a maximum angle of deviation to one another of 20 degrees, more preferably 10 degrees, even more preferably 5 degrees, and most preferably 3 degrees.

In further preferred examples the apparatus allows the distance between the ultrasonic transducer 2 and the ultrasonic receiver 3 to be adapted and preferably further comprises a blocking element 9 defining a minimum distance between the ultrasonic transducer or the ultrasonic receiver to enable them to be positioned at very close proximity to one another but otherwise prevent them from touching.

In a preferred example, the ultrasonic transducer and the ultrasonic receiver of the measuring unit are respectively coupled to rigid arms 5 and 6 which are connected to each other by a connecting element 7. This effectively results in an arrangement like a pair of tongs with the ultrasonic transducer and ultrasonic receivers arranged at the ends of the two arms. At least one of the two arms is preferably pivotably coupled with the connecting element. The aforementioned blocking element may preferably be located between the pivotal point 8 and the ultrasonic transducer or the ultrasonic receiver.

In a further example, a guidance element may be provided which prevents the possibility of shearing movements of the ultrasonic transducer 2 and the ultrasonic receiver 3 against each other. The guidance element is preferably located between the pivotal point and the ultrasonic transducer or the ultrasonic receiver.

According to another example, at least one of the two arms is configured to be laterally adjustable or parallelly moveable with respect to the other one of the two rigid arms and/or at least one of the two arms is preferably cranked.

In accordance with the aforementioned examples, the ultrasonic transducer and the ultrasonic receiver are preferably movable or adjustable in the horizontal and/or the vertical direction.

According to second aspect of the invention, similar to the aforementioned first aspect, an apparatus is provided comprising a measuring unit 4 for performing TAU for locating cavitations in a jawbone, wherein the measuring unit comprises an ultrasonic transducer 2 and an ultrasonic receiver 3 and the apparatus comprises means to ensure good acoustical conductivity. The means include at least one of:

a) a preferably semi-solid gel having a sound velocity in a range of 1460 m/s to 1615 m/s, a sound attenuation in the range of 0.3 dB/cm to 1.5 dB/cm (1 MHz) and/or a haul-off speed for spontaneous resilience of at most 80 mm/sec, the gel being preferably fixed to the transducer and/or the receiver;

b) a flexible cover filled with a liquid or gel, preferably water, in such a manner that the cover can be squeezed into any direction, wherein the flexible cover is preferably fixed to the transducer and/or receiver; and c) a flexible and elastic balloon filled with a liquid or gel in such a manner that the balloon is can be squeezed into any direction.

The flexible cover preferably comprises two pockets connected to each other, the two pockets holding the ultrasonic receiver and the liquid filling, respectively, and wherein the flexible cover is preferably a single-use article.

The apparatus according to the second aspect may also include any of the aforementioned exemplary additional features disclosed with respect to the first aspect. The apparatus may also preferably further comprise at least one light emitting diode (LED) and/or at least one camera and/or at least one attitude sensor to aid positioning around the jawbone.

In a further example, the ultrasonic transducer 2 and/or the ultrasonic receiver (3) are covered by a single-use cover which preferably does not interfere with measurements performed by the measurement unit.

In a third aspect of the present invention, an ultrasonic receiver 3 is provided for use in an apparatus 1 comprising a measuring unit 4 for performing TAU for locating cavitations in a jawbone, the measuring unit comprising an ultrasonic transducer 2 and the ultrasonic receiver 3, wherein the ultrasonic receiver 3 is configured so that a minimum distance between an outer surface of the ultrasonic receiver and a plurality of active piezoelectric elements 11 therein is preferably half the size of a single one of the plurality of active piezoelectric elements. In other words, at least some of the active piezoelectric elements are at very close proximity the outer rim of the ultrasonic receiver such that the distance between the edge of some of the active piezoelectric elements and the rim is less than the size of the active element itself. This can be seen in FIG. 2 and shall be discussed in more detail below. Such an ultrasonic receiver 3 is preferably used as the ultrasonic receiver 3 of the aforementioned apparatuses according to the first and second aspects of the invention.

In a preferred example, the active piezoelectric elements of the ultrasonic receiver are hexagonal and are formed on a film and arranged in a hexagonal formation, wherein the film is preferably made of polyvinylidene fluoride, PVDF. This technique makes best use of surface area of receiver, enables a high degree of coverage of the surface of the receiver with the active piezoelectric elements, eliminates dead space, maximises number of sensor elements that can be formed in a small area, and also enables programming of the elements in accordance with a field-programmable gate array of a main unit for processing signals generated by the ultrasonic receiver. Furthermore, measurement may be performed in a plurality of cycles, for example, by performing measurement with groups of sensors in each hexagonal segment in sequence.

Figure 2:
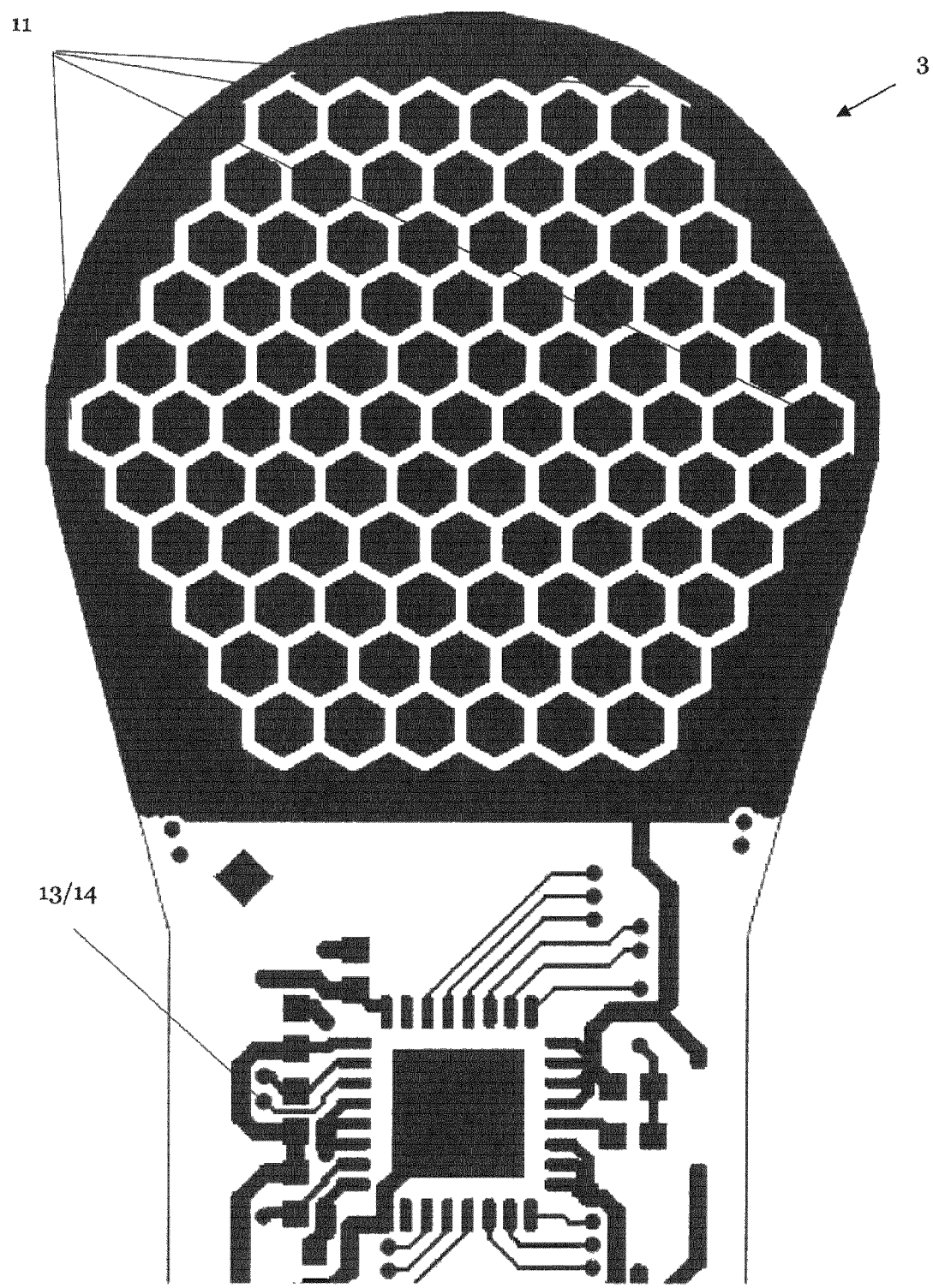
FIG. 2 shows an example of an ultrasonic receiver 3 according to a third aspect of the invention, wherein the active piezoelectric elements 11 of the ultrasonic receiver are hexagonal and are formed on a film and arranged in a hexagonal formation. According to the example shown in FIG. 2, the ultrasonic receiver 3 is configured so that the minimum distance between the outer surface of the ultrasonic receiver 3 and four active piezoelectric elements 11 therein is half the size of a single one of the four active piezoelectric elements 11. Furthermore, a circuit including an amplifier 13 and a multiplexer 14 is shown.

According to another preferred example as shown in FIG. 2, the ultrasonic receiver 3 is configured so that the minimum distance between the outer surface of the ultrasonic receiver and four active piezoelectric elements 11 therein is half the size of a single one of the four active piezoelectric elements 11.

According to further preferred examples, the aforementioned apparatuses preferably further comprise a flexible strip configured to measure a force applied to at least one of the arms and wherein the apparatus is configured to provide an indication of the measured force by visual and/or audible means. By preferably locating a flexible strip in the arm of the apparatus coupled to the ultrasonic receiver, this example prevents excessive force from being applied to the gel interface between the ultrasonic transducer and ultrasonic receiver. Furthermore, an LED or display preferably provides an indication of force being applied to the apparatus and preferably the level of such force being applied by a user to at least one of the arms of the apparatus.

According to a further example, in response to the measured force exceeding or falling below one or more predetermined thresholds, the apparatus is preferably configured to provide an indication according to the value of measured force or control operation of the apparatus. The apparatus can display and/or emit audible alarm if the measured force exceeding a predetermined threshold which may, for example, indicate the proximity of the ultrasonic transducer and receiver to one another is too low, or turn off the apparatus if the measured force falls below a predetermined threshold (i.e. indicating that the user is not actively using the apparatus) to reduce unnecessary power consumption.

According to a further example, the aforementioned apparatuses preferably further comprise means configured to measure the angle between the ultrasonic transducer and ultrasonic receiver. The angle between the ultrasonic transducer and receiver may be defined as the angle between the two rigid arms, at least one of which is movable with respect to the other. The means is preferably configured to measure the angle for each measurement performed by the apparatus. This angle data is preferably saved for each measurement and may subsequently be used to evaluate and avoid measurement errors. This data can also be used to derive values for distances between the ultrasonic transducer and receiver and/or together with the force measurements to provide further context for evaluation and the mitigation of erroneous measurements upon further processing.

In a further preferred example, the aforementioned apparatuses further comprise an amplifier 13 or means configured to amplify analogue signal data generated by the ultrasonic receiver. By amplifying analogue signal data prior to transmission, high signal strength and a reduction in errors due to weak signals can be mitigated.

In a further preferred example, the above apparatuses further comprise a multiplexer 14 or means configured to multiplex the analogue signal data generated by the ultrasonic receiver. The amplification means and/or the multiplexing means is preferably located in the arm to which the ultrasonic receiver is coupled and in close proximity to the ultrasonic receiver in order to improve signal-to-noise ratio i.e. to reduce error.

In another preferred example, the apparatuses further comprise a transmitter or means to transmit the multiplexed analogue signal data to a discrete main unit that is separate from but associated with the apparatus for further processing of the signals. Due to the multiplexing, the number of transmission means from the apparatus to the main unit is beneficially smaller than the number of active piezoelectric elements in the ultrasonic receiver. By multiplexing the analogue signal data received simultaneously from a plurality of all the active piezoelectric elements (e.g. 96 elements), in a wired example i.e. when the transmission means comprises a plurality of cables, the apparatus advantageously reduces the number of cables required for transmitting the preprocessed signal data to the main unit (e.g. 8 cables as opposed to 96) and thereby enables serial transmission and processing of the signal data. In a wireless embodiment i.e. when the transmission means is a wireless transmitter, the apparatus would similarly reduce the number of channels needed for transmitting the multiplexed signals wirelessly to the main unit, thereby making efficient use of transmission resources.

In a further example of the aforementioned apparatuses including the means to ensure good acoustical conductivity, the means are fixed to an active side of the ultrasonic transducer and are of a thickness of between 3 and 6 times the thickness of the ultrasonic transducer. By including a relatively thick gel layer on the transmitting surface of the ultrasonic transducer compared to its own thickness, this example enables easy manipulation i.e. changing the angle of the transducer in order to measure difficult i.e. non-uniform anatomical structures.

Figure 3:
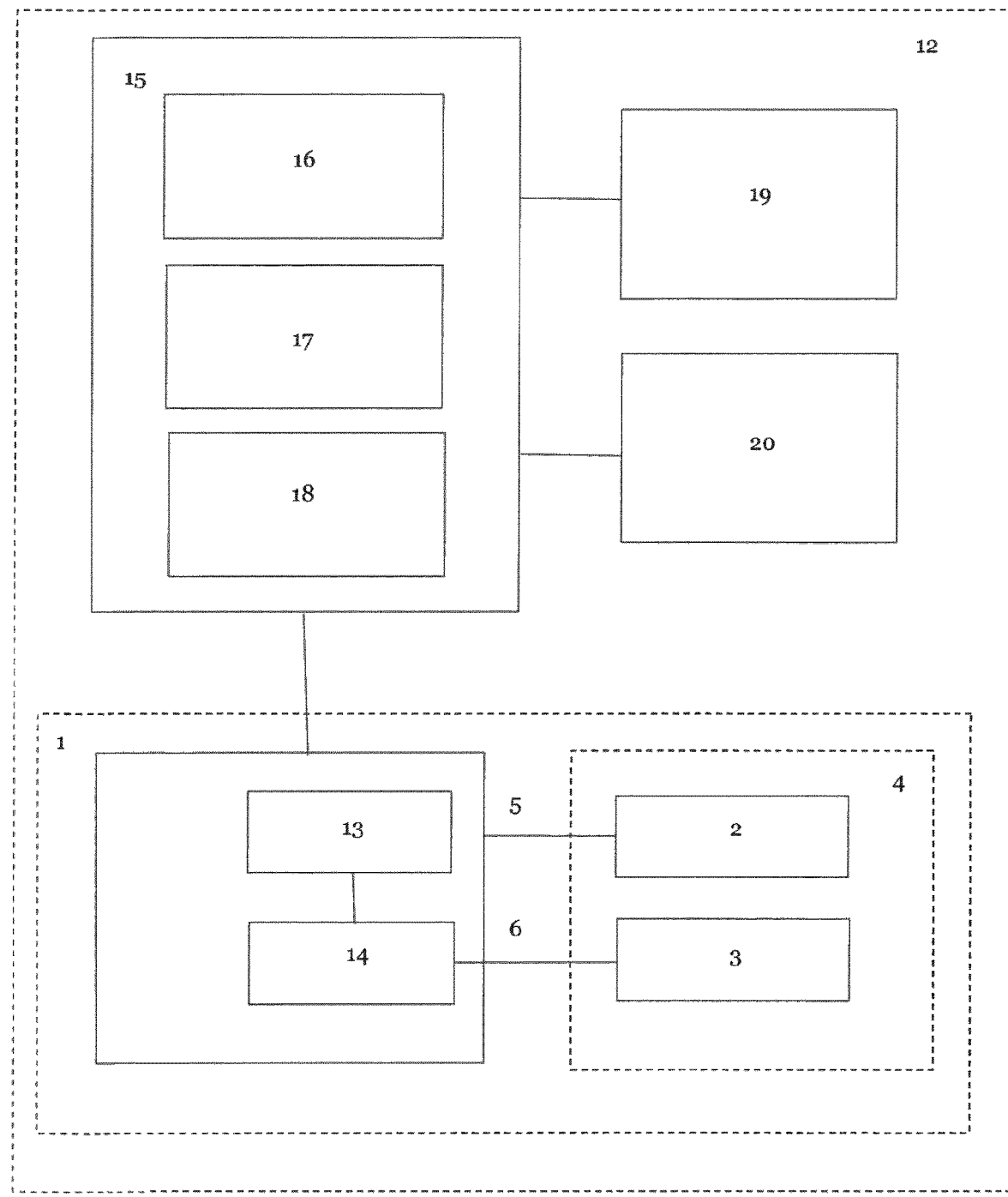
FIG. 3 shows an exemplary implementation of a system 12 according to a fourth aspect of the invention, wherein the system comprises the hand-held apparatus 1 according to the first and/or second aspects of the invention, wherein the apparatus 1 further comprises an amplifier 13 to amplify analogue signal data generated by the ultrasonic receiver 3 and a multiplexer 14 preferably located in the rigid arm 6 in close proximity to the ultrasonic receiver 3 in order to improve signal-to-noise ratio i.e. to reduce error. The exemplary system shown in FIG. 3 further includes a main unit 15 comprising a processing means 16 configured to digitalise the multiplexed analogue signal data and a memory 17 configured to store the multiplexed analogue signal data, and means for generating a high voltage 18 configured to transmit pulses of a desired frequency to the apparatus.

According to a further fourth aspect of the invention as shown in FIG. 3, a system 12 is provided comprising the aforementioned apparatuses according to the first and/or second aspects of the invention and including a main unit 15 comprising a processing means 16 configured to digitalise the multiplexed analogue signal data and a memory 17 configured to store the multiplexed analogue signal data, and means 18 for generating a high voltage configured to transmit pulses of a desired frequency to the apparatus 1. The system may further include a server 19 for storing measured and processed data connected to the main unit by wired or wireless means and/or a display unit 20 also connected to the main unit by wired or wireless means.

In a fifth aspect of the invention, a method for determining the absence and/or presence and location of cavitations in a jawbone is provided, preferably using one of the aforementioned apparatuses or preferred examples thereof. In such a method, acoustical conductivity is preferably established by the use of ultrasonic gels and/or the use of the tongue of the patient.

In one example, the method further comprises the steps of transmitting the amplified and multiplexed analogue signal data to a processing means in a discrete main unit associated with the apparatus concurrently with digitalising the signal data; partially processing the digital signal data; storing the partially processed signal data in a memory; and transmitting the partially processed digital signal data to a software application for final processing and subsequent transmission to a display unit associated with the apparatus. By storing all the raw signal data separately from the (partially) processed e.g. digitalised signal data, this enables subsequent signal processing based on raw data in order to, for example, change i.e. improve resolution of TAU image.

In a preferred example, the method includes simultaneously receiving the analogue signal data of groups of piezoelectric elements in sequence; multiplexing and amplifying the analogue signal data generated by the ultrasonic receiver. By splitting the signal data into smaller portions in this manner, preprocessing may be facilitated. Furthermore, this enables serial processing of signals from e.g. 8 active piezoelectric elements during a cycle. However, on each cycle, non-neighbouring active piezoelectric elements are preferably used to ensure good spread or distribution of measurements. For example, 12 cycles may be performed for a total of 96 piezoelectric elements. This approach offers the advantage of avoiding possible crosstalk between elements during processing and thus serves to reduce the error and increase the resolution.

In a further preferred example, the method includes a step of displaying the further processed data by associating different signal strengths with at least one of: a grayscale comprising different tones, one or more colour schemes comprising different colours and a graph, preferably wherein signal data for unproblematic zones are displayed with reduced coloured areas whilst data indicating peculiarities are displayed as large areas. By providing one or more grayscale/colour schemes, this aids a user with recognition of relevant data. Furthermore, displaying the signal data in a form of graph enables quick diagnosis. Such a graph can be presented in 2D format e.g. a stacked bar chart or in 3D. By measuring, for example, a fundamental wave of 2.5 MHz and, for example the third harmonic at 7.5 MHz, this example of the present invention enables initial analysis of the fundamental wave values only as this requires less processing resources. Further, the values for the third harmonic may subsequently be analysed. Such measurements and analysis can be used to form a graph which may, for example, indicate the presence of a fast wave which shows a potential cavitation. Optionally, the signal data can also be displayed in a plan view wherein signals for unproblematic zones of the jawbone are displayed with reduced coloured areas whilst peculiarities are shown with large areas, thereby aiding diagnosis.

In another preferred example, the further processed data may be displayed by superimposing it over an x-ray image of the jawbone area being measured using TAU. This beneficially provides more context for diagnosis and improves recognition of relevant data.

Finally, a method for calibrating and testing the proper functioning of an apparatus in accordance with the aforementioned descriptions is provided wherein the method comprises performing a plurality of ultrasonic measurements successively in media with different and known acoustical properties and comparing the results of the performed ultrasonic measurements with default values. For ease of calibration, two stark contrasting mediums may be used for such calibration, for example, initially performing ultrasonic measurements in water and then removing the transducer and receiver from the water and continuing to perform measurements in air as the second medium.

The invention claimed is:

1. An apparatus comprising:
a measuring unit for performing through-transmission alveolar ultrasonography (TAU) for locating cavitations in a jawbone, wherein the measuring unit comprises:
an ultrasonic transducer; and
a round ultrasonic receiver, the apparatus being configured to define the geometric position of the ultrasonic transducer and the ultrasonic receiver with respect to each other, wherein the ultrasonic transducer is coupled to an arm and the ultrasonic receiver of the measuring unit is coupled to another arm, wherein the arms are connected to each other by a connecting element, wherein the arms are rigid, and wherein at least one of the arms is pivotably coupled with the connecting element,
wherein the apparatus allows the distance between the ultrasonic transducer and the ultrasonic receiver to be adapted and further comprises a blocking element defining a minimum distance between the ultrasonic transducer and the ultrasonic receiver, and wherein the blocking element is located between a pivot point and the ultrasonic transducer or the ultrasonic receiver;
wherein the apparatus further comprises:
means configured to multiplex analog signal data generated by the ultrasonic receiver,
wherein the multiplexing means is located in the arm to which the ultrasonic receiver is coupled and in close proximity to the ultrasonic receiver, and
further comprising means to transmit the multiplexed analog signal data to a discrete main unit associated with the apparatus for further processing,
wherein a number of transmission means from the apparatus to the discrete main unit is smaller than a number of active piezoelectric elements in the ultrasonic receiver.

2. The apparatus according to claim 1, wherein the ultrasonic transducer and the ultrasonic receiver each define a plane and the apparatus is further configured to arrange the respective planes in positions substantially opposite and/or substantially facing each other.

3. The apparatus according to claim 2, wherein, during use, the planes have a maximum angle of deviation to one another of 20 degrees.

4. The apparatus according to claim 1, further comprising a guidance element which allows substantially avoidance of shearing movements of the ultrasonic transducer and the ultrasonic receiver against each other, wherein the guidance element is located between the pivotal point and the ultrasonic transducer or the ultrasonic receiver.

5. The apparatus according to claim 1, wherein at least one of the two arms is configured to be laterally adjustable or parallelly moveable with respect to the other one of the two rigid arms, wherein at least one of the two arms is cranked.

6. The apparatus according to claim 1, wherein the ultrasonic transducer and the ultrasonic receiver are movable or adjustable in a horizontal and/or a vertical direction.

7. The apparatus of claim 1, further comprising means to ensure acoustical conductivity, wherein the means to ensure acoustical conductivity includes at least one of:
    a) a semi-solid gel having a sound velocity in a range of 1460 m/s to 1615 m/s, a sound attenuation in the range of 0.3 dB/cm to 1.5 dB/cm and/or a haul-off Speed for spontaneous resilience of at most 80 mm/sec, the gel being fixed to the transducer and/or the receiver;
    b) a flexible cover filled with a first liquid or gel, in such a manner that the flexible cover can be squeezed into any direction, wherein the flexible cover is fixed to the ultrasonic transducer and/or the ultrasonic receiver; and
    c) a flexible and elastic balloon filled with a second liquid or gel in such a manner that the balloon can be squeezed into any direction,
        wherein the flexible cover comprises two pockets connected to each other, the two pockets holding the ultrasonic receiver and the liquid filling, respectively, and wherein the flexible cover is a single-use article, further
        comprising at least one light emitting diode (LED) and/or at least one camera and/or at least one attitude sensor.

8. The apparatus according to claim 7, wherein the means to ensure good acoustical conductivity is fixed to an active side of the ultrasonic transducer and has a thickness of between 3 and 6 times a thickness of the ultrasonic transducer.

9. The apparatus according to claim 1, wherein the ultrasonic transducer and/or the ultrasonic receiver are covered by a single-use cover which does not interfere with measurements performed by the measurement unit.

10. The apparatus according to claim 1, further comprising a flexible strip configured to measure a force applied to at least one of the arms and wherein the apparatus is configured to provide an indication of the measured force, wherein the indication is provided by visual and/or audible means, wherein the apparatus is configured to, in response to the measured force exceeding or falling below one or more predetermined thresholds, provide the indication according to a value of measured force or control operation of the apparatus.

11. The apparatus according to claim 1, further comprising means configured to amplify the analog signal data generated by the ultrasonic receiver.

12. The apparatus according to claim 1, wherein the apparatus is handheld.

13. A method for determining an absence and/or presence and location of the cavitations in the jawbone using the apparatus according to claim 11, wherein acoustical conductivity is established by use of ultrasonic gels and/or the use of a tongue of a patient, the method comprising:
    receiving analog signal data of groups of piezoelectric elements in sequence;
    multiplexing and amplifying the analog signal data generated by the ultrasonic receiver;
    transmitting the amplified and multiplexed analog signal data to a processing means in a discrete main unit associated with the apparatus concurrently with digitalizing the amplified and multiplexed signal data;
    partially processing the digital signal data;
    storing the partially processed signal data in a memory; and
    transmitting the partially processed digital signal data to a software application being run by the processing means for final processing and subsequent transmission to a display unit associated with the apparatus,
    wherein the method further comprises steps of:
        displaying further processed data by associating different signal strengths with at least one of: a grayscale comprising different tones, one or more color schemes comprising different colors and a graph, wherein signal data for unproblematic zones are displayed with reduced colored areas whilst data indicating peculiarities are displayed as large areas, and
        displaying the further processed data by superimposing the further processed data over an x-ray image of a jawbone area being measured.

14. The method according to claim 13, further comprising measuring a force applied to at least part of the apparatus and providing an indication of the measured force, and, in response to the measured force exceeding or falling below one or more predetermined thresholds, providing an indication according to a value of measured force or controlling operation of the apparatus.

15. A system comprising:
    an apparatus comprising a measuring unit for performing through-transmission alveolar ultrasonography (TAU) for locating cavitations in a jawbone, wherein the measuring unit comprises an ultrasonic transducer and a round ultrasonic receiver, the apparatus being configured to define the geometric position of the ultrasonic transducer and the ultrasonic receiver with respect to each other, wherein the ultrasonic transducer is coupled to an arm and the ultrasonic receiver of the measuring unit is coupled to another arm, wherein the arms are connected to each other by a connecting element, wherein the arms are rigid, and wherein at least one of the arms is pivotably coupled with the connecting element, wherein the apparatus allows the distance between the ultrasonic transducer and the ultrasonic receiver to be adapted and further comprises a blocking element defining a minimum distance between the ultrasonic transducer and the ultrasonic receiver, and wherein the blocking element is located between a pivot point and the ultrasonic transducer or the ultrasonic receiver, wherein the apparatus further comprises:
    means configured to multiplex analog signal data generated by the ultrasonic receiver,
    wherein the multiplexing means is located in the arm to which the ultrasonic receiver is coupled and in close proximity to the ultrasonic receiver, and further comprising means to transmit the multiplexed analog signal data to a discrete main unit associated with the apparatus for further processing,
wherein a number of transmission means from the apparatus to the discrete main unit is smaller than a number of active piezoelectric elements in the ultrasonic receiver; and
a main unit comprising:
processing means configured to digitalize the multiplexed analog signal data; and
a memory configured to store the multiplexed analog signal data.

16. A method for calibrating and testing the proper functioning of an apparatus comprising a measuring unit for performing through-transmission alveolar ultrasonography (TAU) for locating cavitations in a jawbone, wherein the measuring unit comprises an ultrasonic transducer and a round ultrasonic receiver, the apparatus being configured to define the geometric position of the ultrasonic transducer and the ultrasonic receiver with respect to each other, wherein the ultrasonic transducer is coupled to an arm and the ultrasonic receiver of the measuring unit is coupled to another arm, wherein the arms are connected to each other by a connecting element, wherein the arms are rigid, and wherein at least one of the arms is pivotably coupled with the connecting element, wherein the apparatus allows the distance between the ultrasonic transducer and the ultrasonic receiver to be adapted and further comprises a blocking element defining a minimum distance between the ultrasonic transducer and the ultrasonic receiver, and wherein the blocking element is located between a pivot point and the ultrasonic transducer or the ultrasonic receiver, wherein the apparatus further comprises means configured to multiplex analog signal data generated by the ultrasonic receiver, wherein the multiplexing means is located in the arm to which the ultrasonic receiver is coupled and in close proximity to the ultrasonic receiver, and further comprising means to transmit the multiplexed analog signal data to a discrete main unit associated with the apparatus for further processing, wherein a number of transmission means from the apparatus to the discrete main unit is smaller than a number of active piezoelectric elements in the ultrasonic receiver, the method comprising performing a plurality of ultrasonic measurements successively in media with different and known acoustical properties and comparing the results of the performed ultrasonic measurements with default values.

* * * * *